(12) United States Patent
Prausnitz et al.

(10) Patent No.: US 7,273,458 B2
(45) Date of Patent: Sep. 25, 2007

(54) METHOD OF APPLYING ACOUSTIC ENERGY EFFECTIVE TO ALTER TRANSPORT OR CELL VIABILITY

(75) Inventors: Mark R. Prausnitz, Decatur, GA (US); Jin Liu, Atlanta, GA (US); Thomas N. Lewis, Seattle, WA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1301 days.

(21) Appl. No.: 09/229,226

(22) Filed: Jan. 12, 1999

(65) Prior Publication Data

US 2002/0082527 A1 Jun. 27, 2002

Related U.S. Application Data

(60) Provisional application No. 60/085,304, filed on May 13, 1998, provisional application No. 60/071,240, filed on Jan. 12, 1998.

(51) Int. Cl.
  *A61N 7/00* (2006.01)
(52) U.S. Cl. .............................. 601/2; 604/22; 604/28; 604/501
(58) Field of Classification Search ................ 600/309, 600/439; 601/2–4; 604/20, 22, 28, 500, 604/501, 290, 49
  See application file for complete search history.

(56) References Cited

U.S. PATENT DOCUMENTS

| | | | |
|---|---|---|---|
| 5,445,611 A | 8/1995 | Eppstein et al. | |
| 5,636,632 A | 6/1997 | Bommannan et al. | |
| 5,656,016 A | 8/1997 | Ogden | |
| 5,846,517 A | 12/1998 | Unger | |
| 6,028,066 A | 2/2000 | Unger | |
| 6,033,645 A | 3/2000 | Unger et al. | |
| 6,090,800 A | 7/2000 | Unger et al. | |
| 6,113,559 A * | 9/2000 | Klopotek ........................ 601/3 |

OTHER PUBLICATIONS

Bao, et al., "Transfection of a reporter plasmid into cultured cells by sonoporation in vitro," *Ultrasound Med. Biol.* 23:953-59 (1997).
Barnett, et al., "Current status of research on biophysical effects of ultrasound," *Ultrasound Med. Biol.* 20: 205-18 (1994).
Brayman, et al., "Hemolysis of albunex-supplemented, 40% hematocrit human erythrocytes in vitro by 1-MHz pulsed ultrasound: acoustic pressure and pulse length dependence," *Ultrasound Med. Biol.* 22:927-38 (1996).
Ciaravino, et al., "Pulsed Enhancement of acoustic cavitation: a postulated model," *Ultrasound Med. Biol.* 7:159-66 (1981).
Coleman & Saunders, "A review of the physical properties and biological effects of the high amplitude acoustic field used in extracorporeal lithotripsy," *Ultrasonics* 31:75-89 (1993).
Everbach, et al., "Correlation of ultrasound-induced hemolysis with cavitation detector output in vitro," *Ultrasound Med. Biol.* 23:619-24 (1997).

Exposure Criteria for Medical Diagnostic Ultrasound: I. Criteria Based on Thermal Mechanisms (NCRP Report No. 113), National Council on Radiation Protection and Measurements (Bethesda, MD 1992).
Fechheimer, et al., "Transfection of mammalian cells with plasmid DNA by scrape loading and sonication loading," *Proc. Natl. Acad. Sci. USA* 84:8463-67 (1987).
Gambihler, et al., "Permeabilization of the plasma membrane of L1210 mouse leukemia cells using lithotripter shock waves," *J. Membr. Biol.* 141:267-79 (1994).
Holmes, et al., "Altered neutrophil permeability following shock wave exposure in vitro," *J. Urol.* 147:733-37 (1992).
Jeffers, et al., "Dimethylformamide as an enhancer of cavitation-induced cell lysis in vitro," *J. Acoust. Soc. Am.* 97:669-76 (1995).
Kim, et al., "Ultrasound-mediated transfection of mammalian cells," *Human Gene Ther.* 7:1339-46 (1996).
Kimura, et al., "Standardization of ultrasonic power for sonochemical reaction," *Ultrasonics Sonochem.* 3:S157-S161 (1996).
Kober, et al., "Effect of the pulse length of ultrasound on cell membrane damage in vitro," *J. Acoust. Soc. Am.* 86:6-7 (1989).
Kost & Langer, "Ultrasound-mediated transdermal drug delivery" in *Topical Drug Bioavailability, Bioequivalence, and Penetration* (Shah & Maibach (eds.), pp. 91-104 (Plenum Press, New York 1993).
Leighton, *The Acoustic Bubble* (Academic Press, London 1994).
Margulis, "Kinetics of the number of cavitation bubbles in an ultrasonic field," *Sov. Phys. Acoust.* 22:145-47 (1976).

(Continued)

*Primary Examiner*—Ruth S. Smith
(74) *Attorney, Agent, or Firm*—Pabst Patent Group LLP

(57) ABSTRACT

A method for reversibly, or irreversibly, altering the permeability of cells, tissues or other biological barriers, to molecules to be transported into or through these materials, through the application of acoustic energy, is enhanced by applying the ultrasound in combination with devices for monitoring and/or implementing feedback controls. The acoustic energy is applied directly or indirectly to the cells or tissue whose permeability is to be altered, at a frequency and intensity appropriate to alter the permeability to achieve the desired effect, such as the transport of endogenous or exogenous molecules and/or fluid, for drug delivery, measurement of analyte, removal of fluid, alteration of cell or tissue viability or alteration of structure of materials such as kidney or gall bladder stones. In the preferred embodiment, the method includes measuring the strength of the acoustic field applied to the cell or tissue at the applied frequency or other frequencies, and using the acoustic measurement to modify continued or subsequent application of acoustic energy to the cell or tissue. In another preferred embodiment, the method further includes simultaneously, previously, or subsequently exposing the cell or tissue to the chemical or biological agent to be transported into or across the cell or tissue. In another preferred application, the method includes removing biological fluid or molecules from the cells or tissue simultaneously, previously or subsequently to the application of acoustic energy and, optionally, assaying the biological fluid or molecules.

3 Claims, 5 Drawing Sheets

OTHER PUBLICATIONS

Matula, et al., "The acoustic emissions from single-bubble sonoluminescence," *J. Acoust. Soc. Am.* 103:1377-82 (1998).

Mitragotri, et al., "Transdermal drug delivery using low-frequency sonophoresis," *Pharm. Res.* 13:411-20 (1996).

Mitragotri, et al., "Ultrasound-Mediated Transdermal Protein Delivery," *Science* 269:850-53 (1995).

Prausnitz, "Transdermal delivery of macromolecules: recent advances by modification of skin's barrier properties" in *Therapeutic Protein and Peptide Formulation and Delivery* (Shahrokh, et al., eds.) pp. 124-153 (American Chemical Society, Washington, DC 1997).

Saad & Hahn, "Ultrasound-enhanced effects of adriamycin against murine tumors," *Ultrasound Med. Biol.* 18:715-23 (1992).

Stewart & Stratmeyer, eds., *An Overview of Ultrasound: Theory, Measurement, Medical Applications, and Biological Effects (FDA 82-8190)* (U.S. Department of Health and Human Services, Rockville, MD 1983).

Suslick, ed., *Ultrasound: Its Chemical, Physical, and Biological Effects* (VCH, Deerfield Beach, FL 1988).

Tachibana & Tachibana, "Albumin microbubble echo-contrast material as an enhancer for ultrasound accelerated thrombolysis," *Circulation* 92(5):1148-50 (1995).

Tachibana, et al., "Enhancement of cell killing of HL-60 cells by ultrasound in the presence of the photosensitizing drug Photofrin II," *Cancer Lett.* 72(3):195-199 (1993).

Williams, "A possible alteration in the permeability of ascites cell membranes after exposure to acoustic microstreaming," *J. Cell Sci.* 12:875-85 (1973).

Wyber, et al., "The use of sonication for the efficient delivery of plasmid DNA into cells," *Pharm. Res.* 14:750-56 (1997).

Zhang, et al., "Efficient transformation of tobacco by ultrasonication," *Biotechnology* 9:996-97 (1991).

* cited by examiner

METHOD OF APPLYING ACOUSTIC ENERGY EFFECTIVE TO ALTER TRANSPORT OR CELL VIABILITY

CROSS-REFERENCE TO RELATED APPLICATIONS

Priority is claimed to U.S. Provisional applications Ser. No. 60/071,240, filed Jan. 12, 1998, and Ser. No. 60/085,304, filed May 13, 1998.

BACKGROUND OF THE INVENTION

The present invention is in the field of controlled application of acoustic energy to tissues and cells, and more particularly to assessment and control of acoustic energy as a means of enhancing the permeability of cell and tissue for administration of chemical or biological agents.

Ultrasound-mediated administration of drugs, genes, and other therapeutic compounds into and across cells and tissues has shown significant potential in target drug delivery. For example, studies have shown that appropriately applied ultrasound can reversibly permeabilize viable cells so that exogenous material can enter those cells without killing them. Ultrasound-enhanced delivery to cells has been demonstrated in vitro by uptake of extracellular fluid (Williams, *J. Cell Sci.* 12: 875-85 (1973)); drugs (Saad and Hahn, *Ultrasound Med. Biol.* 18: 715-23 (1992)); and DNA into both cells (Fechheimer, et al., *Proc. Natl. Acad. Sci. USA* 84: 8463-67 (1987); Kim, et al., *Human Gene Ther.* 7: 1339-46 (1996); Bao, et al., *Ultrasound Med. Biol.* 23: 953-59 (1997); Wyber, et al., *Pharm. Res.* 14: 750-56 (1997)) and plant tissues (Zhang, et al., *Bio/Technology* 2: 996-97 (1991)).

Similarly, acoustic effects of lithotripters have been shown to permeabilize cell membranes. (Holmes, et al., *J. Urol.* 147: 733-37 (1992); Gambihler, et al., *J. Membr. Biol.* 141: 267-75 (1994)). Ultrasound also has been shown to increase transport of small drugs and proteins across skin, which is of interest for topical and systemic transdermal drug delivery (Kost and Langer, "Ultrasound-mediated transdermal drug delivery" in *Topical Drug Bioavailability, Bioequivalence, and Penetration* (Shah & Maibach (eds.)) pp. 91-104 (Plenum Press, New York 1993); Mitragotri, et al., *Pharm. Res.* 13: 411-20 (1996); (Mitragotri, et al., *Science* 269: 850-53 (1995); Prausnitz, "Transdermal delivery of proteins: recent advances by modification of skin's barrier properties" in *Therapeutic Protein and Peptide Formulation and Delivery* (Shahrokh, et al., eds.) pp. 124-53 (American Chemical Society, Washington, D.C. 1997)).

Ultrasound has been a well established diagnostic and therapeutic tool in medicine for decades (Stewart and Stratmeyer, eds., *An Overview of Ultrasound. Theory, Measurement, Medical Applications, and Biological Effects* (FDA 82-8190) (U.S. Department of Health and Human Services, Rockville, Md. 1983); Suslick, ed., *Ultrasound: Its Chemical, Physical, and Biological Effects* (VCH, Deerfield Beach, Fla. 1988)). Ultrasonic imaging is widely used at high frequency and low intensity conditions, which are believed to cause no or minimal effects on cells (Barnett, et al., *Ultrasound Med. Biol.* 20: 205-18 (1994)). Ultrasound also is used therapeutically at somewhat greater intensities to heat tissues for physical therapy and other hyperthermia treatments (*Exposure Criteria for Medical Diagnostic Ultrasound: I. Criteria Based on Thermal Mechanisms* (NCRP Report No. 113), National Council on Radiation Protection and Measurements (Bethesda, Md. 1992)). Under a very different conditions (that is, a spectrum of lower frequencies and high intensity), routine lithotripsy procedures use focused acoustic energy to noninvasively shatter kidney stones so the fragments can be excreted by the body without surgery (Coleman and Saunders, *Ultrasonics* 31: 75-89 (1993)). Kidney stone destruction by lithotripsy is believed to be mediated by cavitation. Tachibana, et al., *Cancer Lett.* 78(1-3): 177-181 (1994); *Cancer Lett.* 72(3): 195-199 (1993) have reported on the use of topically applied ultrasound in combination with a photosensitizer to kill tumor cells and on the combination of topically applied ultrasound in combination with gas containing microspheres to enhance lysis of thrombi, in *Circulation* 92(5): 1148-1150 (1995) and U.S. Pat. No. 5,315,998 to Tachibana, et al.

Acoustic cavitation involves the creation and oscillation of gas bubbles in a liquid (Leighton, *The Acoustic Bubble* (Academic Press, London (1994)). During the low-pressure portion of an ultrasound wave, dissolved gas and vaporized liquid can form gas bubbles. These bubbles then shrink and grow in size, oscillating in response to the subsequent high-and low-pressure portions of the ultrasound wave, a process referred to as stable cavitation. Transient cavitation occurs at greater acoustic pressures, where bubbles violently implode after a few cycles. This implosion can have a number of effects, including transiently raising the local temperature by hundreds of degrees Celsius and the local pressure by hundreds of atmospheres, emitting light by a poorly-understood phenomenon called sonoluminescence, creating short-lived free radicals, and launching a high-velocity liquid microjet. Cavitation also is believed to be responsible for ultrasonic permeabilization of cells and tissues of interest for pharmaceutical applications (Wyber, et al., *Pharm. Res.* 14: 750-56 (1997); Mitragotri, et al., *Pharm. Res.* 13: 411-20 (1996); Barnett, et al., *Ultrasound Med. Biol.* 20: 205-18 (1994)). Nonetheless, the effects of ultrasound parameters on cavitation and cell membrane permeabilization are not sufficiently understood for development and optimization of acoustic techniques in, for example, controlled drug delivery.

It is therefore an object of this invention to provide quantitative assessment and control of acoustic tissue effects.

It is another object of this invention to provide means for enhancing the controlled transportation of molecules into or across cell or tissue barriers.

It is still another object of this invention to provide means for reversibly or irreversibly altering cell or tissue permeability, thereby regulating transport or cell or tissue properties such as viability or structure.

SUMMARY OF THE INVENTION

A method for reversibly, or irreversibly, altering the permeability of cells, tissues or other biological barriers, to molecules to be transported into or through these materials, through the application of acoustic energy, is enhanced by applying the ultrasound in combination with means for monitoring and/or implementing feedback controls. The acoustic energy is applied directly or indirectly to the cells or tissue whose permeability is to be altered, at a frequency and intensity appropriate to alter the permeability (which includes diffusivity) to achieve the desired effect, such as the transport of endogenous or exogenous molecules and/or fluid, for drug delivery, measurement of analyte, removal of fluid, alteration of cell or tissue viability or alteration of structure of materials such as kidney or gall bladder stones.

In the preferred embodiment, the method includes measuring the strength of the acoustic field applied to the cell or tissue at the applied frequency or other frequencies, and using the acoustic measurement to modify continued or subsequent application of acoustic energy to the cell or tissue. In another preferred embodiment, the method further includes simultaneously, previously, or subsequently exposing the cell or tissue to the chemical or biological agent to be transported into or across the cell or tissue. In another preferred application, the method includes removing biological fluid or molecules from the cells or tissue simultaneously, previously or subsequently to the application of acoustic energy and, optionally, assaying the biological fluid or molecules.

In a preferred embodiment, the acoustic energy is applied at a frequency between about 1 kHz and 20 MHz, and at a peak positive pressure up to 100 atmospheres. The acoustic energy can be applied directly to the tissue or cells where the effect is desired. Alternatively, the acoustic energy can be applied at a site at a distance from the transducer, under conditions designed to result in a desired effect at the distant site. Ultrasound can be applied using non-invasive means (for example, by transdermal application), minimally invasive means (for example, using a catheter), or during surgery or other invasive procedures. the acoustic energy can be applied alone, or in combination with therapeutic or diagnostic agents.

The method can be used in a variety of applications, including drug delivery, including gene therapy, administration of vaccines, and administration of targeted therapeutic or diagnostic agents. detection and/or quantitation of analyte, and destruction of tissues such as cancers, fatty tissue or materials such as kidney or gall bladder stones.

DETAILED DESCRIPTION OF THE DISCLOSURE

Figure 1A:
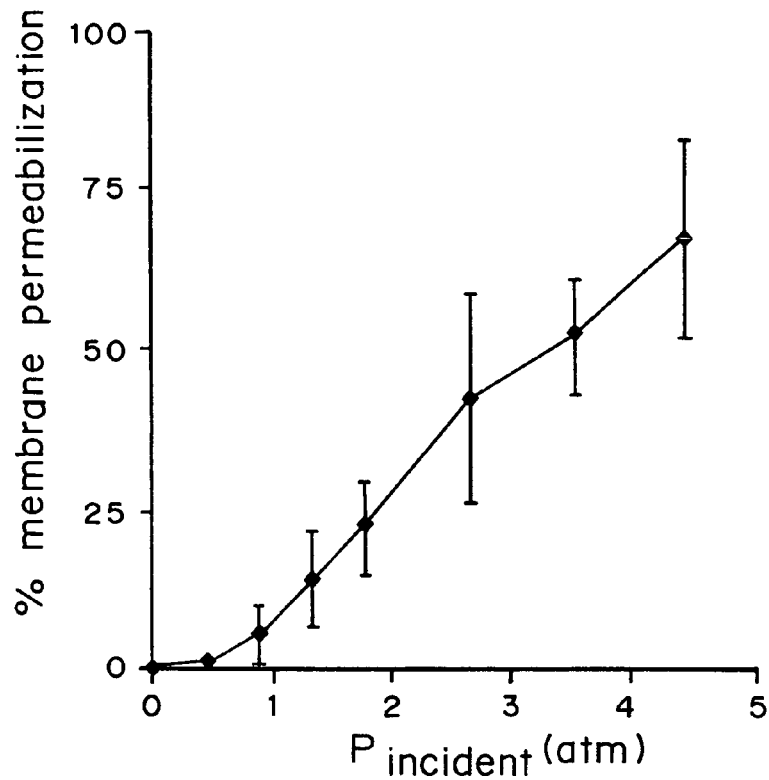
FIGS. 1a and 1b are graphs of incident ultrasonic pressure (1a) and subharmonic pressure (1b) versus percent membrane permeabilization of a suspension of bovine red blood cells exposed to continuous ultrasound for 10 sec. at 24 kHz.

Acoustic energy can be used to cause chemical or biological agents to be transported into and/or across biological barriers, for example, in cells or tissue. Characterizing the dependence of cell membrane permeabilization on acoustic energy conditions is, however, essential to rationally designing acoustic energy protocols for pharmaceutical and other applications. Accordingly, methods are provided herein to use the quantitative dependence of cell membrane permeabilization on various acoustic parameters to enhance the transport of chemical or biological agents to be transported into and/or across biological barriers in cells or tissue, for example, to enhance delivery of drugs to cells in a specific tissue or to increase uptake of compounds which cross cell membranes poorly.

I. Acoustic Energy

As used herein, the term "acoustic energy" means any form of pressure wave, whether audible or inaudible. The frequency of the acoustic energy can be a single frequency or a combination of frequencies. The range of useful frequencies preferably is between about 1 Hz and 100 MHz, and more preferably is between about 1 kHz and 10 MHz and most preferably between 15 kHz and 2 MHz. The waveform of the acoustic energy can be of any shape, including a sinewave or a combination of sinewaves. The pressure of the acoustic energy can be up to a few hundred atmospheres, and preferably is applied at a peak positive pressure of up to 100 atmospheres. The optimal pressure is a function of acoustic frequency and other parameters described below. The acoustic energy can be applied continuously or intermittently.

Acoustic energy can be used to enhance transport by a number of different mechanisms, which broadly fall into two classes. In the first class, acoustic energy directly or indirectly (e.g., via cavitation) provides a driving force for transport. In the second class, acoustic energy increases the permeability of the biological barrier, either reversibly, partially reversibly, or irreversibly. These two mechanisms can be used independently or in combination. In the preferred embodiment, both mechanisms are used simultaneously.

In the first class, where acoustic energy directly or indirectly provides a driving force for transport, both cavitational and non-cavitational mechanisms can be involved. Under appropriate low frequency, high pressure conditions, acoustic energy can cause cavitation, which is the creation of gas cavities, or bubbles, which oscillate stably in the acoustic field and/or collapse, as can be seen during transient or inertial cavitation. The appropriate conditions will depend on the temperature, gas content, acoustic conditions, viscosity and the other properties of the system and acoustic field. Cavitational and non-cavitational acoustic energy also can provide convective or hydrodynamic driving forces for transport, including acoustic streaming, microstreaming, and local, high-velocity jets caused by transient cavitation. Also, chemical and other changes caused by acoustic energy can alter the local environment, thereby changing local chemical potentials, which can alter the chemical potential driving force for net transport by diffusion.

In the second class, where acoustic energy increases the permeability of the biological barrier, either reversibly, partially reversibly, or irreversibly, both cavitational and non-cavitational mechanisms can be involved. For example, increased permeability can be achieved by heating, thereby increasing diffusivity of the molecules. Increased permeability can also be achieved by altering physical structures within biological barriers, such as re-organizing the structure of lipid bilayers, intercellular junctions, and extracellular matrix. These physical effects can be caused by one or more factors, including bulk heating, cavitation, acoustic streaming, microstreaming, high-velocity jets, mechanical interactions, local heating by cavitation, local pressure increases by cavitation, and chemical effects due to creation of free radicals, or stimulation of other chemical reactions.

Preselected Conditions

Acoustic enhancement can be used to alter transport (typically by altering permeability to the molecules to be transported to the material through which they are to pass) or structural integrity of biological materials. The parameters can be selected prior to application, based on previous studies or empirical results. In a preferred method, however, feedback is obtained so that the acoustic enhancement is modified after the initial application as needed to optimize results as treatment progresses.

Acoustic Measurement Feedback

Feedback can involve measurement of one or more variables. Variables include subharmonic pressure, acoustic parameters, temperature, amount or rate of transport of molecules, extent of cavitation, and degree of permeabilization. In one embodiment, the acoustic energy or pressure is measured at one or more frequencies other than the frequency or frequencies at which the acoustic energy is applied. For example, the acoustic energy or pressure is measured at a frequency or frequencies corresponding to integer multiples of one-half or one-fourth of the frequency applied.

As described in Example 1 below, membrane permeabilization is mediated by cavitation, so that subharmonic pressure can be used as a noninvasive way to determine the degree of permeabilization resulting from exposure to acoustic energy. In addition, permeabilization caused by ultrasound should be well predicted by the acoustic parameter $\tau \cdot P_{f/2}$, which characterizes the total cavitational exposure by accounting for both the strength of the f/2 cavitation signal and the time over which it acts.

In a preferred embodiment, the method of enhancing transport of chemical or biological agents across or into a biological barrier includes the following steps:

(a) applying acoustic energy to the biological barrier, for example, the cells or tissue, at one or more frequencies;

(b) measuring the strength of the acoustic field applied to the cells or tissue at the applied frequency or other frequencies; and (c) using the acoustic measurement obtained in step (b) to modify continued or subsequent application of acoustic energy to the cells or tissue.

For example, in a preferred embodiment, a device applies ultrasound to a tissue and the f/2 signal is measured to assess the degree to which the tissue was permeabilized. This information can be used to estimate the amount of drug delivered. Measurement of the f2 signal provides a method for real-time feedback so that the ultrasound exposure based on pre-programmed or user-selected drug delivery profiles can be optimized. The technology required for both generating acoustic energy and "listening" to f/2 signals is known in the art, relatively inexpensive when mass produced, and is readily miniaturizable.

II. Chemical or Biological Agents

The methods described herein can be used to enhance transport of essentially any endogenous or exogenous chemical or biological agent for therapeutic, diagnostic, or prophylactic purposes into or across biological barriers. Useful agents include peptides, proteins, sugars, polysaccharides, nucleotides, polynucleotide molecules, and other synthetic organic or inorganic compounds. Representative proteins and peptides include hormones such as insulin, growth factors, and vaccines. Representative polynucleic acid molecules include antisense, aptamers, ribozymes, and genes, plasmids, and viral vectors. Representative synthetic organic or inorganic drugs include anti-inflammatories, antivirals, antifungals, antibiotics and local anesthetics. As used herein, the agents can be molecules or aggregates or other multi-molecular structures, including for example, virus particles or cells, liposomes or other lipid vesicles or emulsions, or particles including nano or microspheres or capsules. For direct application, the drug will typically be administered in an appropriate pharmaceutically acceptable carrier having an acoustic impedance similar to water, such as an aqueous gel, ointment, lotion, or suspension. Alternatively, a transdermal patch can be used as a carrier.

A variety of analytes are routinely measured in the body fluids such as blood, interstitial fluid, lymph, intracellular fluid or cerebral spinal fluid. Examples of typical analytes that can be measured include blood sugar (glucose), cholesterol, bilirubin, creatinine, vitamin K or other clotting factors, uric acid, carcinoembryonic antigen or other tumor antigens, and various reproductive hormones such as those associated with ovulation or pregnancy. Other analytes that can be measured include alcohol and drugs.

III. Applications

The methods described herein can be used to enhance transport of agents into or across a variety of biological barriers. Representative barriers include mammalian and non-mammalian tissues, including skin, tumor, muscle, lung, brain, heart, blood vessel, bone, cartilage, and internal organs. The tissue or cell can be a part of a living organism, obtained from a living organism, or intended to become part of a living organism, for example, for use in tissue regeneration or tissue engineering, in the form of tissue or dissociated cells. Other representative biological barriers include externally accessible barriers, such as skin, the eye (cornea, conjunctiva, sclera), and the mucosa of the nose, mouth, rectum and vagina, as well as internal barriers, such as the gastrointestinal tract and pulmonary mucosa, blood and lymphatic vessel walls (including the blood-brain barrier), internal organs, tumors, and bones. The barrier can be in the form of intercellular junctions, extracellular matrices, or cell membranes for introduction of material into or out of the interior of a cell or cells. In one preferred embodiment, the biological barrier is human skin.

As used herein, the phrase "biological barrier" encompasses cell membranes, tissue, tissue membranes, intracellular membranes, and biological materials such as kidney stones. It is understood that the technology can be applied directly or indirectly to these materials.

The methods of enhancing transport can be performed with acoustic energy parameters that are preselected and/or that are adjusted based on acoustic measurement feedback.

Acoustic enhancement can preceed, occur simultaneously, or follow treatment with other agents which may be used in combination with the ultrasound to affect transport. For example, chemical enhancers that increase solubility of the materials to be transported, permeability enhancers, or even other driving forces such as mechanical or physical forces (vacuum, pressure, electrical forces) may be used with the ultrasound.

Acoustic enhancement which is administered to enhance transport out of cells or tissues, for example, for measurement of analyte, is administered in an amount which is effective, alone or in combination with other transport enhancers, to extract analyte for detection or quantitation. Acoustic enhancement which is administered to enhance transport of fluid out of tissue or cells is administered in an amount which is effective, alone or in combination with other transport enhancers, to extract fluid, for example, as required to reduce swelling or shrink tissue for easier extraction using other methods or to facilitate breakdown of structural integrity.

Acoustic enhancement which is administered to degrade structural integrity or kill cells is administered in an amount effective to dissociate cells or tissue or other material such as a kidney or gall bladder stone (usually formed of calcium and/or lipid materials) or to irreversibly alter the cell permeability so that the cells become unviable.

Acoustic enhancement which is administered to enhance transport is administered directly or indirectly as required to alter the rate or extent of transport. Enhancement may be measured by an increase in transport, for example, using a marker such as blood levels following transdermal delivery, or through an end result, for example, following introduction of genes into tissue, by expression of the product encoded by the genes.

The transport methods described herein can be used to alter transport as part of a variety of procedures. Acoustic energy can be focused on the target tissue, using an invasive, minimally-invasive, or non-invasive method, to increase transport locally without significantly affecting other tissues. In a preferred embodiment, acoustic energy is applied non-invasively using one or more transducers to focus energy onto the body surface or at a site deeper in the body. In another preferred embodiment, a minimally-invasive method is used, in which, for example, one or more transducers are attached to a laproscopic device for the treatment of tissue accessible from the gastrointestinal tract in, for example, the treatment of colon cancer, or to a catheter for the treatment of tissue accessible from the vasculature in, for example, the treatment of atherosclerosis or restinosis. An invasive approach can be used to treat any tissue. For example, the acoustic energy can be applied in conjunction with another invasive procedure, such as surgery.

In a preferred embodiment, transdermal delivery of a drug, such as insulin, is enhanced by the use of acoustic energy to cause compounds to be transported into and/or across the skin. In another preferred embodiment, a biological material, such as glucose, is transported out of the body through/from the skin using a method facilitated by acoustic energy.

In a similar preferred embodiment, a drug is delivered from outside the body to its interior, or a molecule from inside the body to the exterior, across barriers other than skin, such as the epithelia of the eye, nose, mouth, rectum, or vagina, using a method facilitated by acoustic energy.

In another preferred embodiment, acoustic energy is used to enhance targeted drug delivery by selectively increasing transport of a drug into a target tissue, such as the brain or a tumor. Some tissues, such as tumors, are particularly resistant to transport. Accordingly, acoustic energy can significantly enhance delivery of drug to those tissues.

Other compounds, particularly larger macromolecules, are especially difficult to drive into cells or tissue of any type. The transport of these compounds also can be enhanced by application of acoustic energy. For example, in gene therapy, a target tissue could be treated with acoustic energy to facilitate delivery of DNA into cells.

The compositions and methods of preparation and use thereof described herein are further described by the following non-limiting examples.

EXAMPLE 1

Exposure of Bovine Red Blood Cells to Ultrasound

The dependence of cell membrane permeabilization on ultrasound parameters was determined and the acoustic signals which correlate with observed membrane permeabilization were identified.

Experimental Methods

Bovine red blood cells were exposed to ultrasound at 24 kHz over a range of controlled conditions. The degree of membrane permeabilization was measured by release of hemoglobin and was determined as a function of ultrasound parameters and measured acoustic signals.

Sample Preparation

Freshly drawn bovine blood with Alsevers anticoagulant (Rockland, Gilbertsville, Pa.) was stored at 4° C. for up to 10 days. Red blood cells were collected by centrifugation (GS-15SR, Beckman Instruments, Palo Alto, Calif.; 400 g, 10 min., 4° C.); washed three times with phosphate-buffered saline (PBS; pH 7.4; Sigma, St. Louis, Mo.); and then suspended in PBS at a red blood cell concentration of 10% by volume. The cell suspension was stored on ice and then gently mixed on a nutator (Innovative Medical Systems, Ivyland, Pa.) immediately before use in an experiment.

The cell suspension was added to a sample tube, which was prepared by cutting a 15 ml polypropylene centrifuge tube (VWR, Suwanee, Ga.) at the 4 ml line. After the sample tube was filled with 4 ml of the cell suspension, a rubber stopper (VWR) was carefully inserted into the tube to the 3 ml line, thereby spilling out about 1 ml of the suspension. This procedure was used so that the tube could be sealed without entrapping air bubbles. A hydrophone (Baylor School of Medicine, Houston, Tex.) also was inserted through a small hole in the center of the rubber stopper and positioned at the center of the sample volume.

Exposure to Ultrasound

The ultrasound exposure chamber consisted of a cylindrical piezoelectric transducer (lead zirconate titanate, 5 cm OD, 4.5 cm ID, 2.5 cm length; Channel Industries, Santa Barbara, Calif.) sandwiched between two 10 cm lengths of 1.5 inch Schedule 40 poly(vinyl chloride) (PVC) pipe. The bottom of the chamber was sealed on a clear polycarbonate base (LEXAN™, General Electric, Mt. Vernon, Ind.). The chamber was filled with water which was filtered/deionized (Type III; U.S. Filter, Roswell, Ga.) and degassed using a vacuum chamber (Nalgene, Rochester, N.Y.; pump: 2107VA20A, Thomas, Sheboygan, Wis.).

The sample tube was placed in the water bath within the ultrasound exposure chamber, positioned at the axial and radial center of the transducer, and exposed to low-frequency (24 kHz) ultrasound at room temperature (22±2° C.). A function generator (DS345, Stanford Research Systems, Sunnyvale, Calif.) was programmed to provide a sinewave of selected voltage, duty cycle, burst length, and total exposure time. The output was fed to an amplifier (Macrotech 2400, Crown, Elkhart, Ind.), the signal of which went through a matching transformer (MT-56R, Krohn-Hite, Avon, Mass.) to drive the transducer.

Measurement of Ultrasound Pressure

Figure 2:
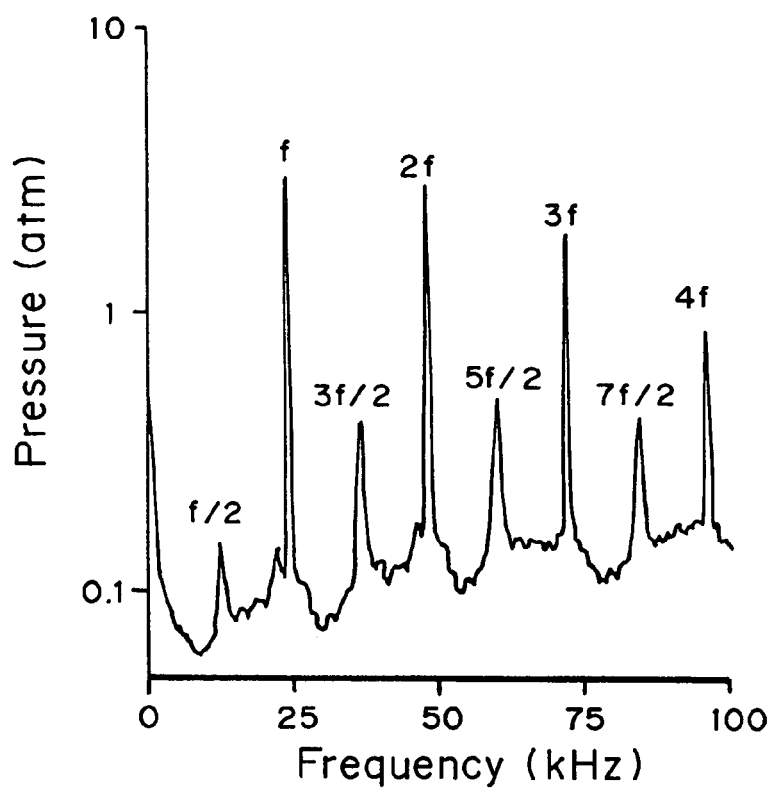
FIG. 2 is a graph of ultrasound frequency versus pressure, which illustrates a representative acoustic spectrum measured during an ultrasound exposure at f=24 kHz, which caused extensive cavitation.

To monitor the ultrasound exposure, the voltage applied to the transducer was measured with an oscilloscope (54603B, Hewlett Packard, Santa Clara, Calif.). This voltage was used to estimate the incident ultrasound pressure, as described below. In addition, the signal from the hydrophone in the sample tube was fed to the oscilloscope and a spectrum analyzer (SR760, Stanford Research Systems), which was used to determine the amplitude of different acoustic signals shown in FIG. 2 and Table 1. Higher harmonics of f (e.g., 2f=48 kHz) are seen in FIG. 2, due to cavitation and apparatus resonance. Cavitation also generates other signals, including the subharmonic (f/2=12 kHz) and its ultraharmonics (e.g., 3f/2=36 kHz) and an elevated broadband "noise" level (e.g., b1, b2). The acoustic spectrum measured during exposure of cells to ultrasound provided information about cavitation and its effects on membrane permeability, as described below.

The strength of ultrasound is reported as its incident pressure. The incident pressure is defined as the pressure level that would exist in the absence of cavitation, which is primarily at the driving frequency (i.e., 24 kHz). The incident pressure is important because one of the effects of cavitation is to shift acoustic energy to frequencies other than the driving frequency, as shown in FIG. 2. Incident pressure is the most useful means to characterize ultrasound, because it is independent of apparatus geometry and represents the total relevant acoustic input. For propagating wave fields created by a planar transducer at high frequency, ultrasound strength is often reported as an intensity (e.g., in units $W/cm^2$). For ultrasonic irradiation of a surface such as skin with a planar transducer, this approach seems appropriate (Kost and Langer, "Ultrasound-mediated transdermal drug delivery" in *Topical Drug Bioavailability, Bioequivalence, and Penetration* (Shah & Maibach, eds.) pp. 91-104 (Plenum Press, New York 1993)). In this experiment, however, a radially-symmetric standing wave-like field is generated because of the cylindrical geometry of the transducer and because of the use of low frequency ultrasound with a wavelength comparable to the apparatus diameter, which field makes acoustic intensity extremely difficult to determine. Alternatively, the reported pressure can be directly measured with a hydrophone at the driving frequency. While this approach is useful at low acoustic levels where the measured pressure has the same value as the incident pressure, at higher intensities where cavitation occurs, acoustic energy is shifted to a spectrum of other frequencies, as shown in FIG. 2. Thus, the pressure measured at the driving frequency accounts for only a portion of the ultrasound exposure applied to the cells.

The peak incident pressure generated within the exposure chamber was estimated by measuring the acoustic pressure at subcavitation levels and linearly extrapolating to higher drive levels (Matula, et al., *J. Acoust. Soc. Am.* 101: 1994-2002 (1997)). At supra-cavitation levels, the incident pressure continues to increase as a linear function of the voltage, whereas the measured pressure levels off and may decrease due to cavitation. A linear fit of the data was therefore generated only at low pressure (i.e., less than 2.0 atm. for degassed water) for the pressure as a function of transducer voltage:

$$P=0.0089 \cdot V \quad (r^2=0.99) \tag{1}$$

where peak positive pressure (P) has units of atmospheres and peak-to-peak voltage (V) has units of volts. This equation was extrapolated to higher voltages and pressures and was used to convert measured transducer voltages to the incident pressures described in these examples.

Measurement of Ultrasound Power and Heating

Bulk heating caused by ultrasound was measured and determined to be less than 1° C. for all exposures. Using an iron/constantan thermocouple (Model SA1-J thermocouple; Model DP 460 display; Omega Engineering, Stamford, Conn.) inserted into the water bath, which was mixed using a stir bar and magnetic stirrer (VWR), the temperature was determined to rise at 0.17° C./min. during continuous exposure to ultrasound at 2.2 atm. and at 0.73° C./min. at 4.5 atm incident pressure.

Although incident pressure, rather than power, is used to characterize the strength of ultrasound, it should be helpful to know the power of ultrasound exposures used here for comparison with other studies. Assuming that all acoustic energy from the transducer was eventually converted into heat and that heat loss from the apparatus to the surroundings was negligible, the measured heating rates described above can be used to determine the power output of the transducer with the equation $$W = m_{water} \, C_{Pwater} \, dT/dt \tag{2}$$

where W is power, $m_{water}$ is the mass of water in the water bath (0.3 kg), $C_{Pwater}$ is the heat capacity of water (4.18 J/g° C.), and dT/dt is the change of temperature with respect to time (e.g., 0.17° C./min. at 2.2 atm.). For example, this equation yields 3.4 W at 2.2 atm and 15.1 W at 4.5 atm. using the heating rates given provided above. This type of calorimetric method is commonly used to estimate ultrasonic power (Kimura, et al., *Ultrasonics Sonochem.* 3: S157-S161 (1996)).

A second method to determine the power of ultrasound exposures was to measure the electrical power supplied to the transducer. The values determined by the two methods should be equal if there is complete conversion of electrical power to acoustic power by the transducer (i.e., 100% efficiency). The voltage across the transducer was measured directly with an oscilloscope (model 2430A, Tektronics, Beaverton, Oreg.) and the current was measured using a current transformer (Model 2100, Pearson Electronics, Palo Alto, Calif.) and fed to the oscilloscope. The average power was calculated as the average of the product of the current and voltage signals and yielded the following relationship $$W = 0.00010 \cdot V^2 \quad (r^2 = 1.00) \tag{3}$$

where power (W) has units of watts and peak-to-peak voltage (V) has units of volts. Combination of Equations 1 and 3 yields the following equation which relates power to incident pressure for the experimental apparatus used herein:

$$W = 1.3 \cdot P^2 \tag{4}$$

where power (W) has units of watts and incident pressure (P) has units of atmospheres. This equation indicates the power is 6.3 W at 2.2 atm and 26 W at 4.5 atm, which are considerably higher than the values determined using Equation 2. This overprediction is expected, since Equation 4 assumes 100% efficient conversion of electrical energy by the transducer into acoustic energy. In contrast, Equation 2 yields an underprediction, since perfect insulation of the apparatus is assumed. Thus, Equations 2 and 4 provide upper and lower bounds for the acoustic energy.

Post-Exposure Analysis

After exposure to ultrasound, samples were removed from the sample tube and spun down, as described above. The supernatant contained free hemoglobin released from permeabilized cells, while the pellet contained intact cells. The supernatant was collected and the absorbance of hemoglobin in the supernatant was determined at 575 nm using a spectrophotometer (DU-64, Beckman Instruments). As a positive control, the absorbance was also determined for a sample in which all cells were lysed by suspension in deionized water. The ratio of these absorbances yielded the percent hemoglobin released, expressed as percent membrane permeabilization in the Figures described herein.

Results

To develop a rational approach to designing protocols for ultrasound-mediated cell membrane permeabilization, the degree of permeabilization of bovine red blood cells exposed to low-frequency (24 kHz) ultrasound was measured as a function of incident ultrasound pressure, total exposure time, pulse length, and duty cycle. In addition, the amount of permeabilization was correlated with measurable acoustic signals, which is of interest to noninvasive monitoring of ultrasound's bioeffects and elucidation of mechanisms. The degree of permeabilization was measured by release of hemoglobin from erythrocytes.

Figure 1B:
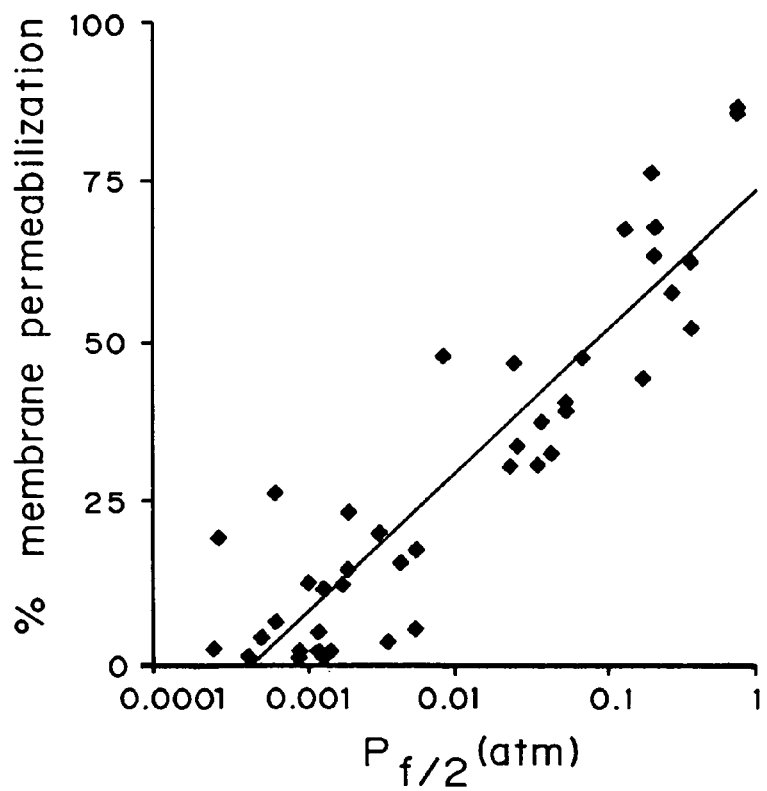

FIG. 1a shows that permeabilization increased with increasing incident pressure (f=24 kHz), a measure of the total ultrasound exposure which cannot be measured directly in the presence of cavitation. Permeabilization exhibited an almost linear dependence for pressures greater than ~0.5 atm, which is consistent with previous studies which show that bioeffects increase with ultrasound pressure or intensity (Stewart & Stratmeyer, eds., *An Overview of Ultrasound: Theory, Measurement, Medical Applications, and Biological Effects* (FDA 82-8190), U.S. Department of Health and Human Services (Rockville, Md. 1983); Suslick, ed., *Ultrasound: Its Chemical, Physical, and Biological Effects* (VCH, Deerfield Beach, Fla. 1988); Barnett, et al., *Ultrasound Med. Biol.* 20: 205-18 (1994); *Exposure Criteria for Medical Diagnostic Ultrasound: I. Criteria Based on Thermal Mechanisms* (NCRP Report No. 113) (Bethesda, Md. 1992)). FIG. 1b shows that permeabilization increased with increasing subharmonic pressure (f/2=12 kHz), a measure of cavitation which can be measured directly. These figures indicate that membrane permeabilization is mediated by cavitation and that measurement of subharmonic pressure may be a noninvasive way to determine the degree of permeabilization (and thereby the amount of drug delivery) resulting from ultrasound exposure.

FIG. 2 shows a representative spectrum of acoustic signals associated with an ultrasound exposure which causes extensive cavitation. A strong signal is seen at the driving frequency, f (i.e., 24 kHz), which is the frequency at which the transducer resonates. Due to cavitation and other effects, there are also strong signals at integer multiples of the driving frequency (e.g., 2f, 3f, and 4f) and at the subharmonic frequency, f/2, and its ultraharmonics (e.g., 3f/2, 5f/2, and 7f/2). The broadband noise pressure between these peaks (e.g., b1 and b2) also is elevated.

It was assessed whether cell membrane permeabilization correlates with any of these features of the acoustic spectrum, as summarized in Table 1. The correlation was strongest for $P_{f/2}$ (i.e., the pressure at f/2) and its ultraharmonics (set 2). FIG. 1b shows this relationship graphically. Permeabilization also correlated with average measurements of broadband noise pressure between the peaks (set 3). The driving frequency itself and its higher harmonics (set 1) showed the weakest correlation. Previous studies have correlated cell damage with $P_{f/2}$ (Jeffers, et al., *J. Acoust. Soc. Am.* 97: 669-76 (1995)) and 20 f (Everbach, et al., *Ultrasound Med. Biol.* 23: 619-24 (1997)). Mechanistic interpretation of these results is provided below. These correlations may provide a useful means for noninvasively measuring cell permeabilization by ultrasound.

Figure 3:
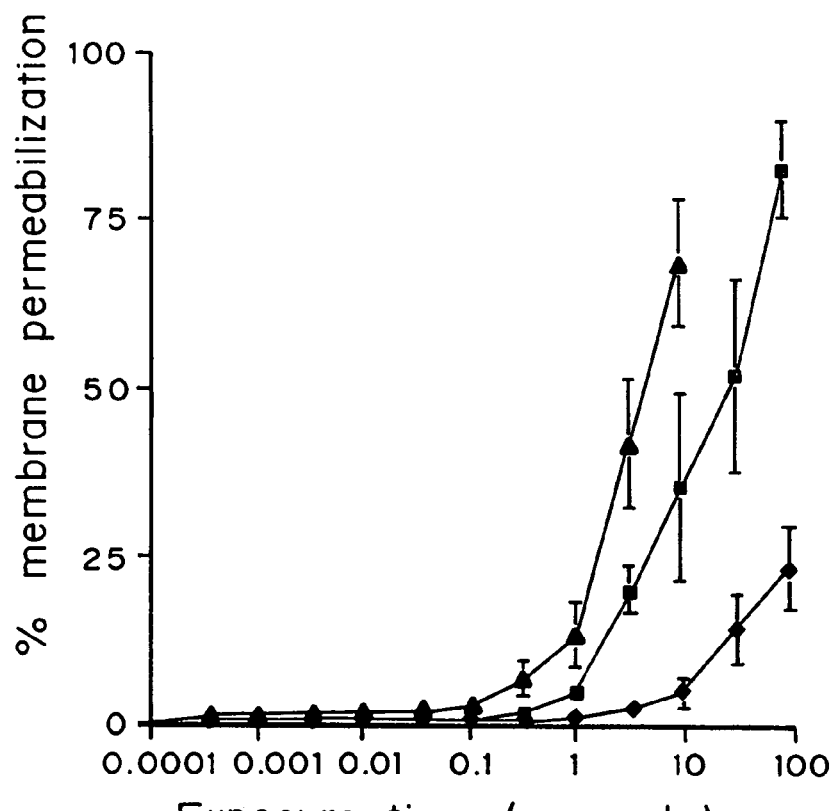
FIG. 3 is a graph of ultrasound exposure time versus percent membrane permeabilization for red blood cells exposed to continuous ultrasound at 24 kHz for different amounts of time at incident pressures of 0.89 atm. (♦), 2.7 atm. (■), and 8.9 atm. (▲).

The effect of total exposure time of a single continuous ultrasound exposure is shown in FIG. 3. In each case, permeabilization increased with exposure time above a threshold of approximately 100 msec. Below approximately 100 msec, ultrasound had little effect on the cells. For longer exposures, membrane permeabilization increased as a strong function of exposure time. This is in qualitative agreement with previous studies conducted under somewhat different conditions, which also show that membrane disruption increases with exposure time above a threshold (Kober, et al., *J. Acoust. Soc. Am.* 86: 6-7 (1989); Brayman, et al., *Ultrasound Med. Biol.* 22: 927-38 (1996)).

Figure 4:
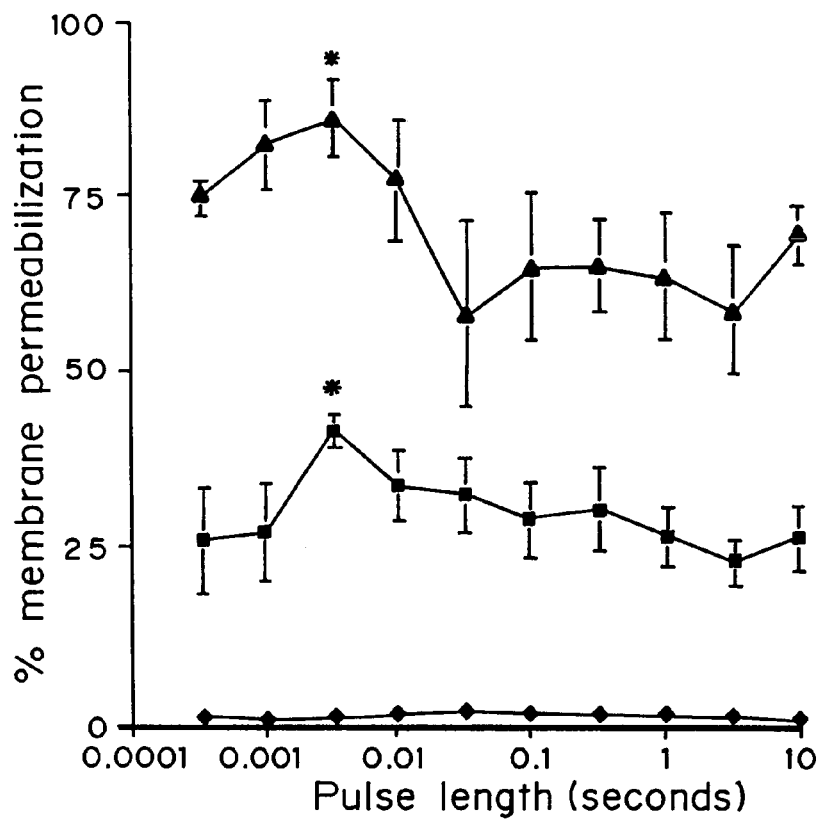
FIG. 4 is a graph of length of time of an ultrasound pulse versus percent membrane permeabilization of cells for pulses applied at a duty cycle of 10% at incident pressures of 0.89 atm. (♦),2.7 atm. (■), and 8.9 atm. (▲).

In FIG. 4, cells were exposed to ultrasound using pulses of different length, but the cumulative "on" time for each set of pulses was kept constant at 10 sec by varying the total number of pulses. Pulses were applied at a duty cycle of 10% and at three different incident pressures: (♦) 0.89 atm., (■) 2.7 atm., and (▲) 8.9 atm. Permeabilization showed a weak dependence on pulse length, with a small, but statistically significant, peak at 3 msec. for both 2.7 atm. and 8.9 atm. ($p<0.05$, by Student's T-test, relative to average permeabilization at pulse lengths $\geq 0.1$ sec). For each pressure tested, the degree of membrane permeabilization varied little as a function of pulse length. There was, however, a small statistically-significant peak in permeabilization at 3 msec. A possible physical explanation for this peak is discussed below.

Figure 5:
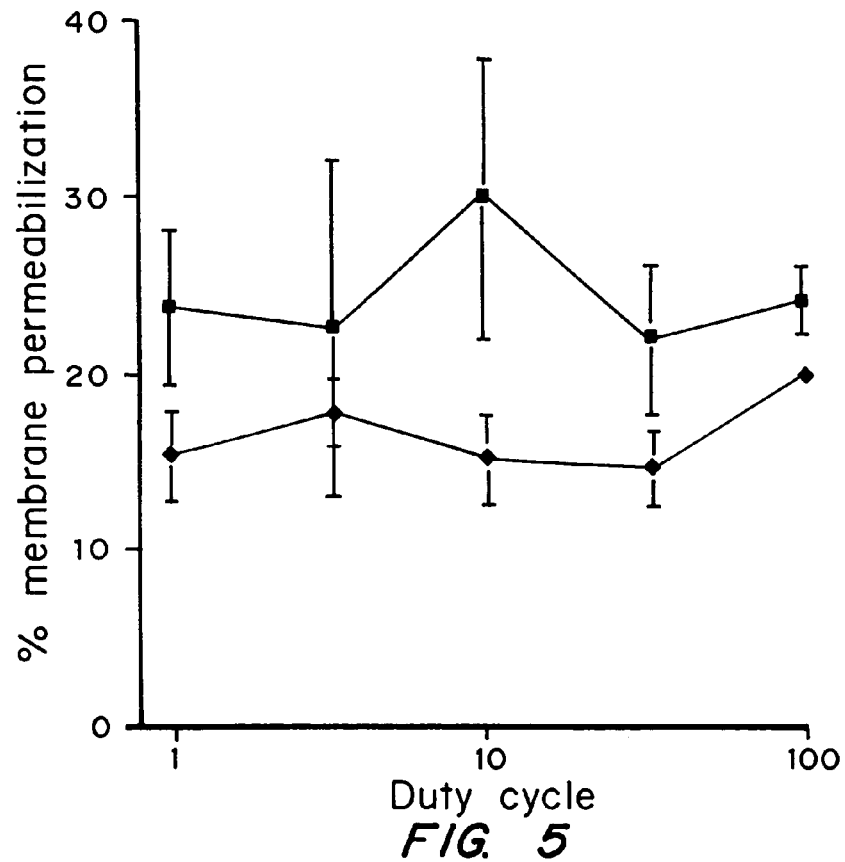
FIG. 5 is a graph of ultrasound duty cycle (%) versus percent membrane permeabilization at an incident pressure of 2.7 atm., for a total "on" time of 10 sec. at a pulse length of 0.1 sec.(♦) or 1 sec. (■).

For pulsed ultrasound, the effect of duty cycle (defined as the fraction of time that the ultrasound is "on" during pulsed application) is shown in FIG. 5. Under the conditions investigated, duty cycle had no significant effect on the degree of membrane permeabilization.

Figure 6:
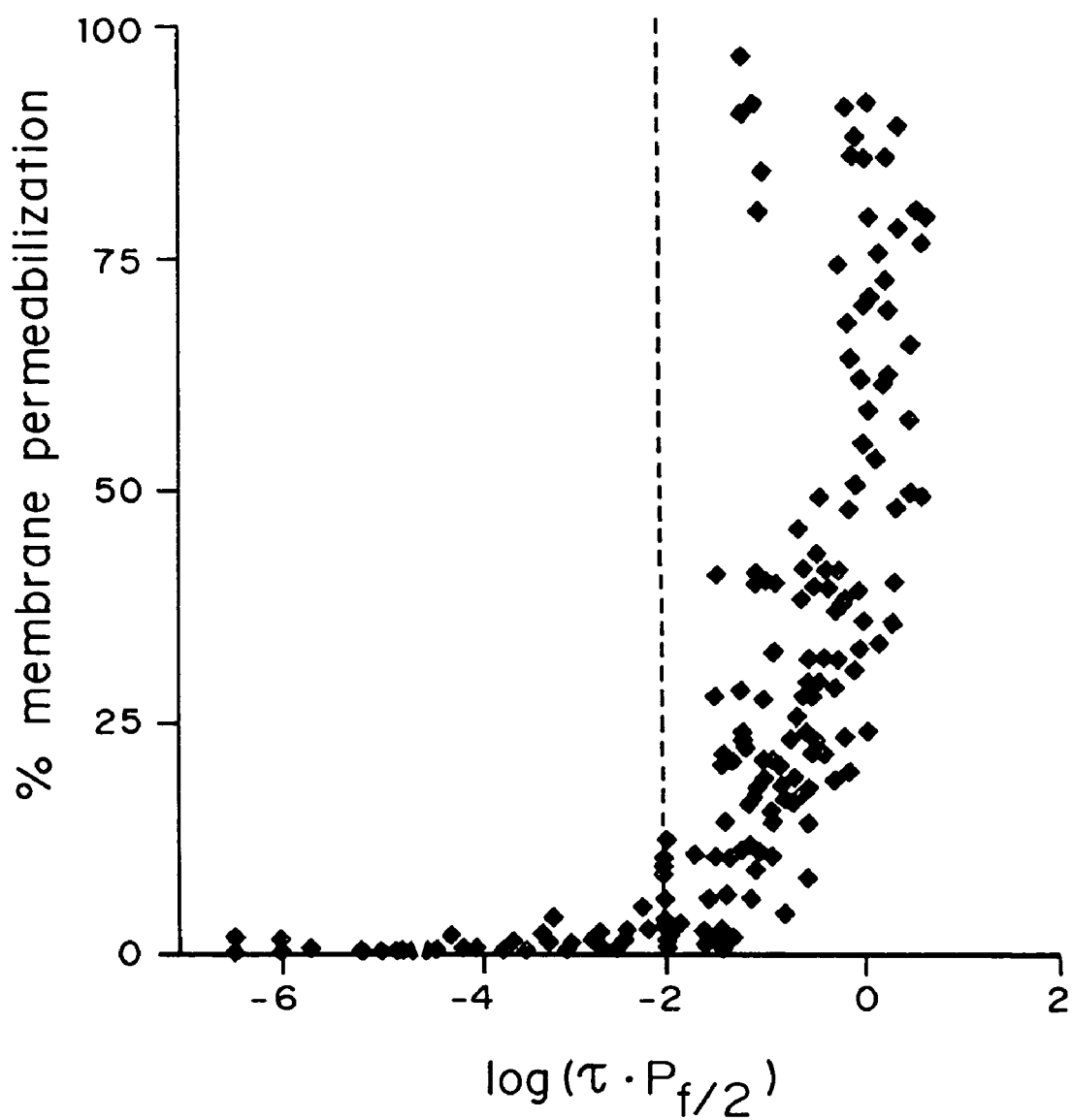
FIG. 6 is a graph of the acoustic parameter $\tau$-$P_{f2}$ versus percent membrane permeabilization, using the data from FIGS. 1-5.

FIG. 1b shows that $P_{f/2}$ is predictive of the degree of membrane permeabilization from exposures of different incident pressure, all having the same pulse length, exposure time, and duty cycle. To generalize the approach and consider exposures of different pulse lengths, exposure times, duty cycles and incident pressures, membrane permeabilization was correlated with the total exposure time ($\tau$), which is equal to the product of pulse length and the number of pulses applied, multiplied by the strength of the f/2 signal ($P_{f/2}$). As shown in FIG. 6, this parameter ($\tau \cdot P_{f/2}$) correlated well with membrane permeabilization, showing a threshold value at approximately 0.01 (i.e., $\log(\tau \cdot P_{f/2}=-2)$. Below this threshold little permeabilization occurred, and above it permeabilization increased sharply. Because FIG. 6 includes all of the data collected in this study and because the parameter $\tau \cdot P_{f/2}$ correlates well with the whole data set, it appears that measurement of this single parameter can provide a simple, non-invasive, and broadly-applicable method for determining membrane permeabilization caused by any acoustic energy exposure.

The parameter $\tau \cdot P_{f/2}$ was chosen because it characterizes the total cavitational exposure by accounting for both the strength of the f/2 cavitation signal ($P_{f/2}$) and the time over which it acts ($\tau$). The good correlation between permeabilization and $\tau \cdot P_{f/2}$ is significant because measurement of this single parameter can provide a simple, non-invasive method for determining membrane permeabilization caused by any ultrasound exposure.

These studies showed that permeabilization increased with incident ultrasound pressure, increased with total exposure time above a threshold of approximately 100 msec, showed a weak dependence on pulse length with a small maximum at 3 msec, and did not depend on duty cycle under the conditions examined. Using measured acoustic spectra, it was found that red blood cell membrane permeabilization correlated best with the pressure measured at half the driving frequency (f/2=12 kHz) and its ultraharmonics, less strongly with the broadband noise pressure measured between peaks, and least strongly with pressure measured at the driving frequency and its higher harmonics. Permeabilization caused by ultrasound applied at any set of conditions tested in this study could be well predicted by the parameter $\tau \cdot P_{f/2}$, which characterizes the total cavitational exposure.

Discussion

Effect of Ultrasound Parameters

This study shows that permeabilization increases as a strong function of incident pressure (FIG. 1) and total exposure time (FIG. 3), which indicates that selection of appropriate pressure and duration of ultrasound exposure is important to achieve permeabilization at a desired level. The existence of a threshold near 100 msec of total exposure time (FIG. 3) also constrains possible protocols. In contrast, the observation that permeabilization depends only weakly on pulse length (FIG. 4) and duty cycle (FIG. 5) is useful, since it permits greater flexibility in designing ultrasound protocols.

The effects of different ultrasound parameters summarized above can be explained in terms of cavitation, the mechanism by which membranes are believed to be disrupted (Barnett, et al., *Ultrasound Med. Biol.* 20: 205-18 (1994); Leighton, *The Acoustic Bubble* (Academic Press, London 1994)). It is well established that at greater acoustic pressure more cavitation bubbles with greater energy are created (Leighton, *The Acoustic Bubble* (1994)). Similarly, longer total exposure times also yield more cavitation bubbles. This increased cavitation should result in more extensive membrane permeabilization, as seen in FIGS. 1 and 3. The minimum exposure time of 100 msec shown in FIG. 3 could result from the "warm-up" time it takes for bubbles to nucleate, grow, and possibly collapse over many ultrasound cycles (Margulis, *Sov. Phys. Acoust.* 22: 145-47 (1976)).

The maximum permeabilization observed for 3 msec pulses in FIG. 4 could be explained by two competing effects involving a mechanism proposed previously (Ciaravino, et al., *Ultrasound Med. Biol.* 7: 159-66 (1981)). Increasing pulse length is advantageous for cavitation because there is more time during each pulse for bubbles to nucleate, grow and collapse. However, it is believed that as pulse length increases so does the time between pulses at constant duty cycle, which means that as the interpulse delay increases, bubbles formed during the previous pulse have time to dissolve back into solution. This mechanism is disadvantageous because it leaves fewer nucleation bubbles available to grow and collapse during the next pulse, which results in less cavitation.

Correlation with Measured Acoustic Signals

Ultrasound causes cavitation which in turn causes effects on cells. Therefore the most useful predictor of ultrasound's effects on cells should be a measure of cavitation. Membrane permeabilization was correlated with measured acoustic signals which are known to be associated with cavitation. A good correlation was found for the pressure measured at half the driving frequency (f/2=12 kHz) and its ultraharmonics (FIG. 1b, set 2 of Table 1). In addition, permeabilization caused by ultrasound applied at any set of conditions tested in this study could be well predicted by the parameter $\tau \cdot P_{f/2}$, which characterizes the total cavitational exposure by accounting for both the strength of the f/2 cavitation signal and the time over which it acts.

Correlation of acoustic signals with membrane permeabilization also provides mechanistic insight. The best correlation was found for the signal at f/2 and its ultraharmonics (set 2 of Table 1, FIG. 1b). This suggests that permeabilization was mediated by cavitation. Onset of the f/2 signals is thought to occur with the onset of cavitation (Leighton, *The Acoustic Bubble* (1994)). As the cavitation activity increases, the f/2 signals also generally increase, but a quantitative relationship between amount of cavitation and $P_{f2}$ has not been established. Cavitation bubbles are thought to give off a signal at f/2 because of a prolonged expansion phase and delayed collapse which can occur during cavitation (Leighton, *The Acoustic Bubble* (1994)). Measurement of f/2 signals at the exact frequency of interest (e.g., 12 kHz; set 2a) yielded a somewhat better correlation with permeabilization than measurement of the signal over the width of the peak (e.g., 11-13 kHz; set 2b).

A reasonable correlation also was established for measurements of broadband signals, or the signals between f, f/2, and higher harmonics (set 3 of Table 1), which also supports a permeabilization mechanism involving cavitation, especially transient cavitation. Upon bubble collapse during transient cavitation, "noise" over a broad spectrum of frequencies is given off, which raises peak and broadband signals alike (Leighton, *The Acoustic Bubble* (1994)). Since both f/2 and broadband signals showed correlation, it appears that both stable and transient cavitation play a role in membrane permeabilization.

Finally, signals at f and its higher harmonics showed the poorest correlation (set 1 in Table 1). This was expected since these signals are related to the non-cavitational driving frequency (f) and resonance of the experimental apparatus (higher harmonics), in addition to stable and transient cavitation. The signal f and its higher harmonics are not expected to be good indicators, since it reflects a mixture of effects.

Conclusion

This study provides a quantitative guide to designing ultrasound protocols useful for drug delivery. The acoustic measurements support the hypothesis that ultrasonic cavitation is the mechanism by which membranes are permeabilized. They also indicate that measurable acoustic signals can provide noninvasive real-time feedback about membrane permeabilization and drug delivery.

Using red blood cells as a model system, it was shown that membrane permeabilization increases with incident ultrasound pressure, increases with total exposure time above a threshold of 100 msec, shows a weak dependence on pulse length with a small maximum at 3 msec, and does not depend on duty cycle under the conditions examined. In addition, the degree of permeabilization was shown to correlate with measurable acoustic signals (e.g., $P_{f/2}$, $\tau \cdot P_{f/2}$), which supports the belief that permeabilization is mediated by cavitation and may provide a method for noninvasive, real-time feedback for an intelligent delivery system.

TABLE 1

Empirical Correlation of Membrane Permeabilization with Measured Acoustic Signals

| | Frequency (kHz)[a] | Correlated Equation[b] | $r^2$[c] |
|---|---|---|---|
| Set 1a | 24 | (f)[d] | M = 19.7 ln (P) + 30.6 | 0.58 |
| | 48 | (2f) | M = 12.4 ln (P) + 43.2 | 0.66 |
| | 72 | (3f) | M = 11.8 ln (P) + 49.2 | 0.58 |
| | 96 | (4f) | M = 11.4 ln (P) + 53.6 | 0.45 |
| Set 1b | 23-25 | (f) | M = 19.7 ln (P) + 65.0 | 0.64 |
| | 47-49 | (2f) | M = 12.7 ln (P) + 64.8 | 0.70 |
| | 71-73 | (3f) | M = 12.3 ln (P) + 68.9 | 0.66 |
| | 95-97 | (4f) | M = 11.7 ln (P) + 69.4 | 0.60 |
| Set 2a | 12 | (f/2) | M = 9.4 ln (P) + 73.0 | 0.84 |
| | 36 | (3f/2) | M = 8.5 ln (P) + 64.7 | 0.85 |
| | 60 | (5f/2) | M = 8.7 ln (P) + 64.4 | 0.85 |
| | 84 | (7f/2) | M = 9.6 ln (P) + 69.6 | 0.85 |
| Set 2b | 11-13 | (f/2) | M = 10.1 ln (P) + 79.8 | 0.81 |
| | 35-37 | (3f/2) | M = 9.0 ln (P) + 70.8 | 0.81 |
| | 59-61 | (5f/2) | M = 9.3 ln (P) + 70.3 | 0.82 |
| | 83-85 | (7f/2) | M = 9.8 ln (P) + 73.1 | 0.82 |
| Set 3 | 13-23 | (b1) | M = 10.2 ln (P) + 82.3 | 0.75 |
| | 25-35 | (b2) | M = 10.5 ln (P) + 82.9 | 0.75 |
| | 37-47 | (b3) | M = 10.2 ln (P) + 80.6 | 0.79 |
| | 49-59 | (b4) | M = 10.6 ln (P) + 78.2 | 0.78 |
| | 61-71 | (b5) | M = 10.3 ln (P) + 78.2 | 0.79 |
| | 73-83 | (b6) | M = 10.6 ln (P) + 79.7 | 0.79 |
| | 85-95 | (b7) | M = 10.2 ln (P) + 77.0 | 0.78 |

[a]Based on spectral information such as that shown in FIG. 2, membrane permeabilization was correlated with the pressure (or the average pressure when a range of frequencies is given) measured at the frequency (or range of frequencies) indicated.
[b]The equation which resulted from a log-linear fit of membrane permeabilization (M) and measured pressure (P) is shown. There is no mechanistic basis for the log-linear functionality; visual inspection suggested it was the most appropriate fit of the data. The units of permeabilization are percent hemoglobin released and the units of pressure are atm.
[c]The $r^2$ correlation coefficient is shown for each fit of the data.
[d]The text in parentheses refers to which harmonic of the driving frequency (f = 24 kHz) the indicated frequencies correspond and "b" indicates a broadband noise measurement.

EXAMPLE 2

Ultrasound-Mediated Disruption of Prostate Tumor Cell Membranes

Introduction

The effects of ultrasound exposure on size, lifetime, and permeability of membrane disruptions in living cells were investigated quantitatively. It was found that ultrasound disruptions were a few nanometers in size, have a lifetime of approximately one minute, and induce extensive molecular uptake.

Methods

Prostate tumor cells (DU-145) were suspended in RPMI-1640 medium with 10% fetal bovine serum at $5\times10^5$ cells/ml. For each experimental condition, a 3 ml polypropylene tube was filled with the cell suspension at room temperature (22±2° C.) and the top of the tube was closed without entrapping any air bubbles. The cells were exposed to ultrasound at 24 kHz in a chamber that consisted of a cylindrical piezoelectric transducer sandwiched between two PVC pipes and filled with deionized and degassed water at room temperature. Pressure, pulse length, duty cycle, and the total exposure time of ultrasound exposure were controlled. Acoustic spectra during exposure were collected using a hydrophone placed in the exposure chamber. Calcein, a green-fluorescent membrane-impermeant marker, dissolved in saline, was added to the suspensions either before or at various times after exposure at a final concentration of 10 µM. Other fluorescent markers, with different sizes, were also used to determine membrane permeability. The cells were kept at room temperature for 15 minutes after exposure, and then placed on ice until they were centrifuged and resuspended in phosphate-buffered saline with 0.1 mg/ml of propidium iodide (a red-fluorescence viability stain). Cell-by-cell fluorescence was measured using flow cytometry, and 6 µm green-fluorescence microspheres were added to each sample at a constant concentration to provide an internal volumetric standard for determining concentrations of viable cells.

Results and Discussion

To better understand how cells are permeabilized by ultrasound, potential mechanisms of membrane disruptions were tested. First, it was observed that cells were permeabilized only in presence of extensive cavitation, as indicated by characteristic changes in measured acoustic spectra (i.e., strong subharmonic and ultraharmonic peaks and broad band noise). Other effects of ultrasound, such as bulk heating and mixing were ruled out as potential mechanisms, since control experiments of heating (up to 2° C., the maximum temperature rise in these experiments) and mixing had negligible effects on cells. Also, cavitation-induced free radicals probably are not responsible, because membrane permeabilization was observed in the presence of free radical scavengers (e.g., 50 µM cysteamine). Therefore, microscale hydrodynamic effects of cavitation probably are the main factor in disrupting cell membranes.

Figure 7:
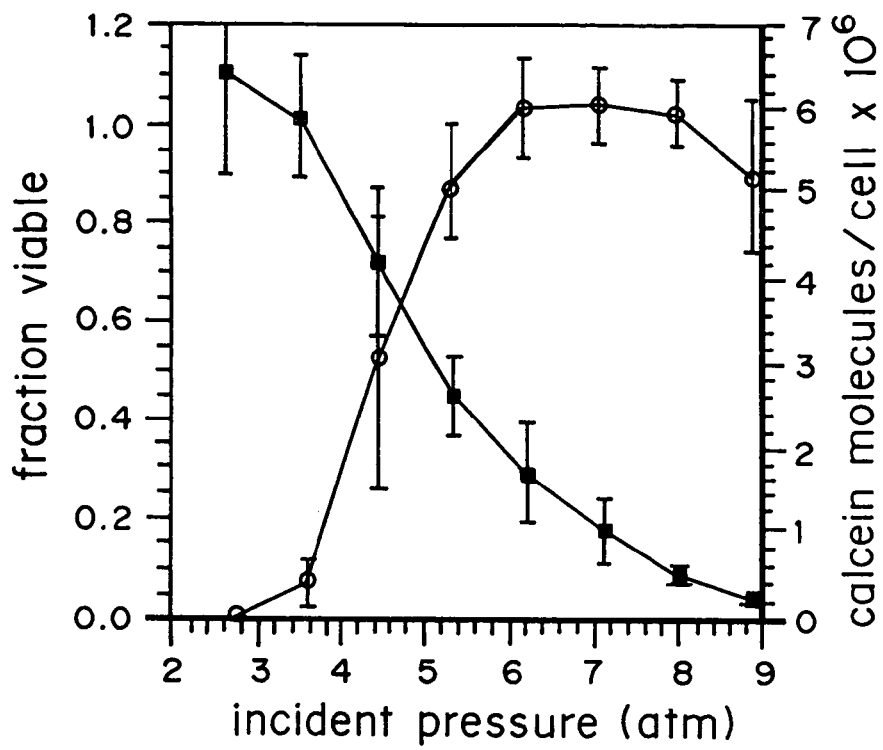
FIG. 7 is a graph showing average uptake of calcein molecules per exposed cell (o) and fraction of viable cells (■) relative to unexposed control, each as a function of peak incident pressure for 20 pulses at 0.1 sec. and 10% duty cycle.

The effects of ultrasound exposure parameters on cell viability and membrane permeabilization (as measured by uptake of calcein added to the cell suspension before exposure) were determined to identify conditions that selectively permeabilize cells without killing them. As peak incident pressure increased, average cellular calcein uptake increased above a threshold and reached a plateau at 20-25% of external calcein concentration (FIG. 7). However, the fraction of viable cells (relative to an unexposed suspension) decreased continuously with increasing pressure (FIG. 7). Uptake increased with total exposure time and reached a plateau at 5 sec. (for P=5.3 atm. and 10 ms pulses at 10% duty cycle), while cell viability decreased continuously. Average uptake showed a small maximum at 10-33 ms and a sharp decline at less than 3 ms, with changes in pulse length from 0.3 ms to 1.0 s. Applied duty cycle (from 0.5% to 80%) did not significantly affect uptake. Fraction of viable cells decreased as uptake increased for most conditions, and was approximately 25% for maximum uptake under optimal conditions.

Membrane disruptions were found to be large enough to allow uptake of bovine serum albumen (radius, r approximately 3.5 nm). Average uptake of BSA molecules per exposed cell was about 60% less than that of calcein (r≈0.7 nm), for the same external concentration (10 µM) and same exposure conditions as given in FIG. 7 (at P=8.0 atm.).

Figure 8:
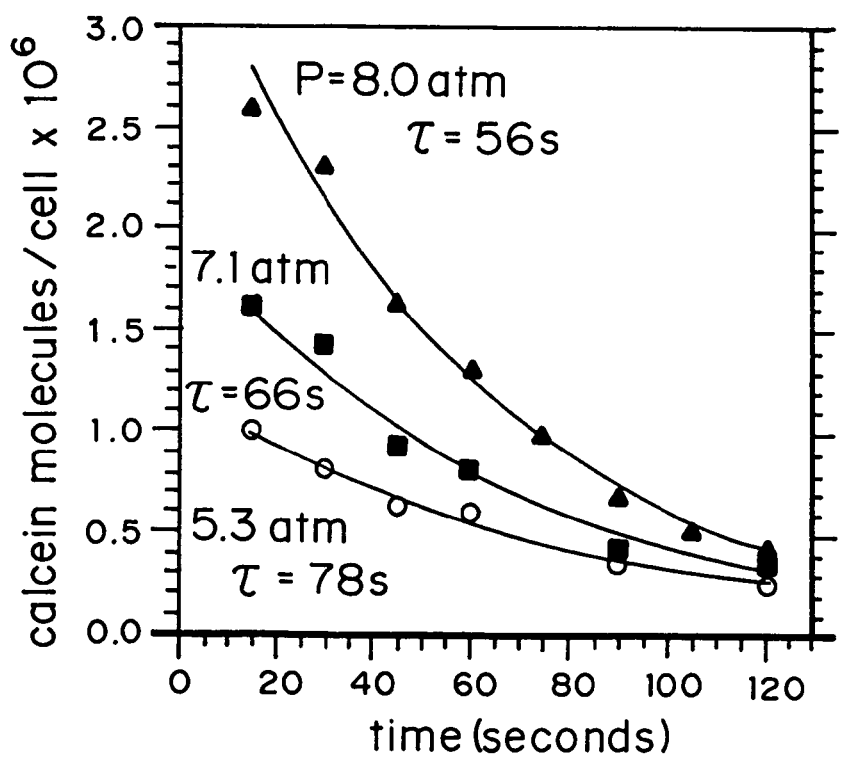
FIG. 8 is a graph showing average uptake of calcein molecules per cell as a function of time at which calcein was added to the cell suspension after exposure.

To determine lifetimes of the membrane disruptions, calcein was added to cell suspensions at different times after ultrasound exposure. As shown in FIG. 8, average uptake of calcein decreased exponentially with time at which calcein was added to a sample ($\geq$15 s after exposure). The data at three incident pressures, 5.3 atm. (o), 7.1 atm. (■), and 8.0 atm. (▲), were fitted with exponential functions, and shown in FIG. 8. The respective time decay constants, τ, at these pressures were 78 sec., 66 sec, and 56 sec., respectively. One can see that the time decay constant, τ, decreased and the initial uptake increased with increasing incident pressure.

Average uptake was about 50% less when calcein was added 15 sec. after exposure compared to when it was added before exposure for the examined pressures. However, significant uptake occurred for up to two minutes after exposure.

Modifications and variations of the present invention will be obvious to those of skill in the art from the foregoing detailed description. Such modifications and variations are intended to come within the scope of the following claims.

We claim:

1. A method for altering cell viability or transport of chemical or biological agents into or through an internal organ, internal tissue or vessel in a human or other animal using acoustic energy, comprising:

administering acoustic energy at one or more frequencies by applying a transducer to a first site on the human or other animal other than where transport or cell viability is to be altered;

wherein the acoustic energy is effective to alter transport or cell viability at a second site distant from the first site at a different tissue or an internal organ or an internal vessel in a different tissue, wherein the transducer is placed inside the body using invasive or minimally invasive means.

2. A method for altering cell viability or transport of chemical or biological agents into or through an internal organ, internal tissue or vessel in a human or other animal using acoustic energy, comprising:

administering acoustic energy at one or more frequencies by applying a transducer to a first site on the human or other animal other than where transport or cell viability is to be altered;

wherein the acoustic energy is effective to alter transport or cell viability at a second site distant from the first site at a different tissue or an internal organ or an internal vessel in a different tissue, wherein the transducer is placed within a blood vessel using a catheter.

3. A method for altering cell viability or transport of chemical or biological agents into or through an internal organ, internal tissue or vessel in a human or other animal using acoustic energy, comprising:

administering acoustic energy at one or more frequencies by applying a transducer to a first site on the human or other animal other than where transport or cell viability is to be altered;

wherein the acoustic energy is effective to alter transport or cell viability at a second site distant from the first site at a different tissue or an internal organ or an internal vessel in a different tissue, wherein the transducer is placed within a surgical incision.

* * * * *